United States Patent [19]

Keller, Jr.

[11] 4,203,448

[45] May 20, 1980

[54] PROGRAMMABLY VARIABLE VOLTAGE MULTIPLIER FOR IMPLANTED STIMULATOR

[75] Inventor: John W. Keller, Jr., Miami, Fla.

[73] Assignee: Biotronik Mess- und Therapiegeräte GmbH & Co., Berlin, Fed. Rep. of Germany

[21] Appl. No.: 917,140

[22] Filed: Jun. 19, 1978

[30] Foreign Application Priority Data

Aug. 19, 1977 [GB] United Kingdom .............. 34916/77

[51] Int. Cl.² .............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,431,912 | 3/1969 | Keller, Jr. | 128/419 PG |
| 3,707,974 | 1/1973 | Raddi | 128/419 PG |
| 3,726,285 | 4/1973 | Bowers et al. | 128/419 PG |
| 3,757,795 | 9/1973 | Anderson | 128/419 PG |
| 3,867,949 | 2/1975 | Schwalm et al. | 128/419 PG |
| 3,926,197 | 12/1975 | Alley | 128/419 PG |
| 3,983,880 | 10/1976 | Kolenik | 128/419 PG |
| 4,023,121 | 5/1977 | Alley | 128/419 PG |
| 4,041,953 | 8/1977 | Anderson et al. | 128/419 PG |
| 4,050,004 | 9/1977 | Greatbatch | 128/419 PG |

FOREIGN PATENT DOCUMENTS

| | | | |
|---|---|---|---|
| 826766 | 1/1960 | United Kingdom | 128/419 PG |
| 1401274 | 7/1975 | United Kingdom | 128/419 PG |
| 374088 | 6/1973 | U.S.S.R. | 128/419 PG |

*Primary Examiner*—William E. Kamm
*Attorney, Agent, or Firm*—Spencer & Kaye

[57] ABSTRACT

A free running oscillator clocks a counter, which produces stimulation control signals at a predetermined counter. An output stage includes transistors, energized by the counter, to issue stimulating pulses having a voltage equal to that across a capacitor in parallel with the output stage. The output capacitor is charged, between output pulses, by successive charge sharing cycles with at least one other capacitor, which is enabled by a stored program word, at a rate determined by the oscillator output cycles.

3 Claims, 1 Drawing Figure

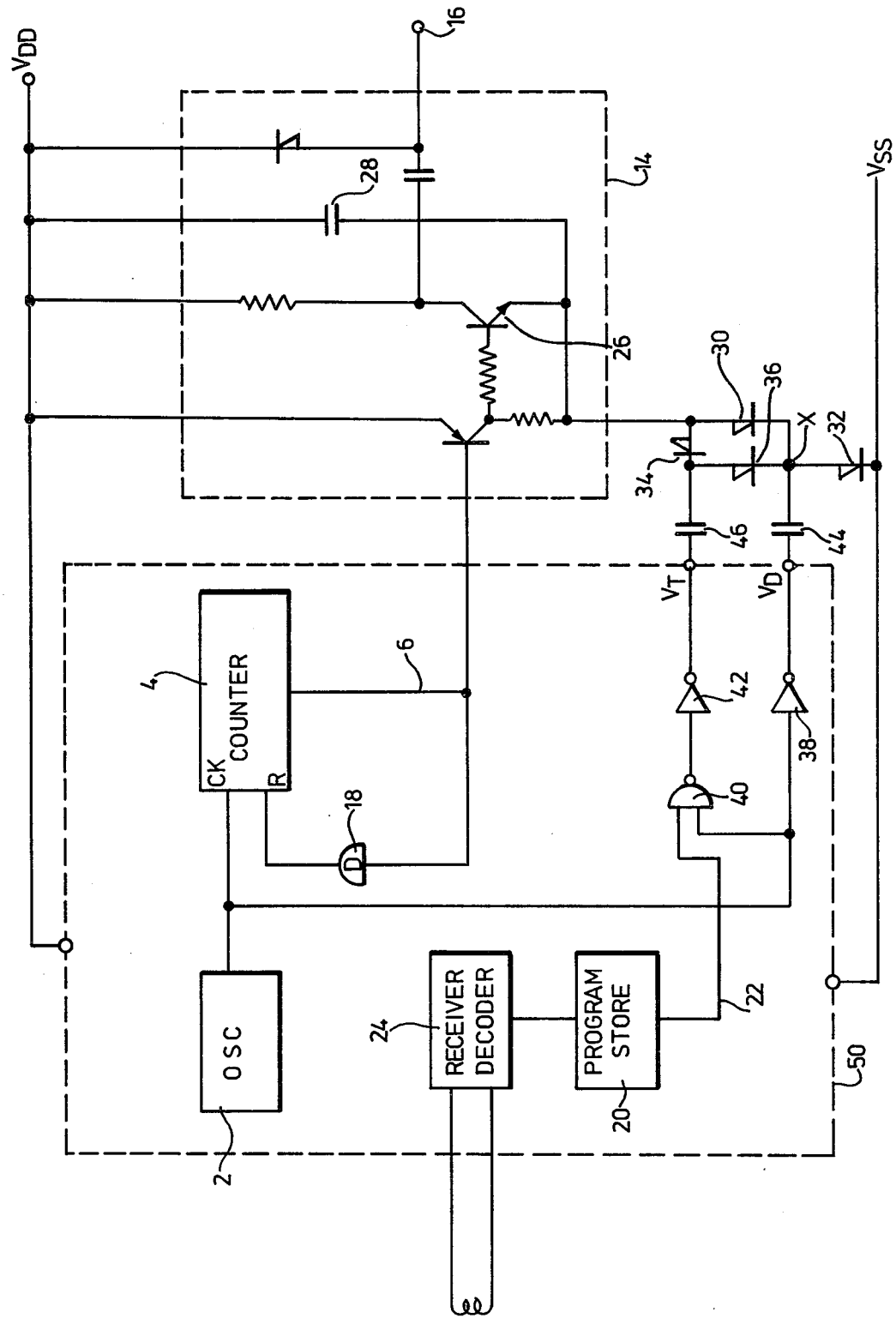

PROGRAMMABLY VARIABLE VOLTAGE MULTIPLIER FOR IMPLANTED STIMULATOR

TECHNICAL FIELD

This invention relates to implantable body function control apparatus and particularly, but not exclusively, to body tissue stimulating devices such as cardiac pacemakers.

BACKGROUND ART

Pacemakers for generating artificial stimulating pulses for the heart, and which may be implanted in the body, are well known. Originally the electrical circuitry for such pacemakers was of analog design, but in recent years digital circuitry has been also employed. A digital approach to pacemakers has led to the evolution of programmable pacemakers—pacemakers having parameters such as pulse rates which are adjustable (programmable) once the pacemaker has been implanted. Programmable pacemakers are described in, for instance, British Pat. Nos. 1,385,954 and 1,398,875. Such pacemakers have circuitry to detect and decode signals transmitted outside the body and alter the program accordingly. In British Pat. No. 1,385,954 (claiming priority based on U.S. Ser. No. 141,694, in turn a parent of U.S. Pat. No. 3,805,796 to Tenz), the programming is accomplished by means of a magnetic field which is sensed by a magnetic reed switch; the opening and closing of the switch providing programming pulses to a program store. In British Pat. No. 1,398,875 (based on U.S. Pat. No 3,833,005 to Wingrove) the programming is by means of radio frequency transmission and reception.

It is desirable to miniaturize pacemaker components as far as possible, especially where implanted pacemakers are concerned, and although integrated circuit techniques can help enormously to achieve this aim, the battery size is still a major problem. The most recently-available miniature batteries having sufficient power and life for pacemaker usage are lithium batteries (both of the "solid" and "viscous" types), and such batteries are now employed in pacemakers. Unfortunately, lithium batteries only generate about 3 volts and although this voltage is sufficient to provide the supply voltage for, say, an integrated circuit pacemaker, it is insufficient, in itself, for the pacemaker output stage which needs to generate artificial stimulating pulses of at least 5 volts. Under certain circumstances, it is even desirable to generate pacing pulses of greater magnitude (e.g. about 7.5 volts). Although two or more lithium batteries can be employed for such purposes (and, indeed, have in the past been so employed), this militates against the desire for maximum miniaturization.

DISCLOSURE OF INVENTION

We have now designed an implantable body function control apparatus which employs a single relatively low voltage source, but which generates, by means of voltage multiplication, the higher voltages for the pacing pulses issued.

According to the invention, there is provided a body function control apparatus comprising an oscillator, means responsive to the oscillator for generating tissue stimulating pulse control signals, an output stage responsive to signals from the control signal generating means for providing tissue stimulating pulses to the body, a voltage source for said apparatus, voltage multiplication means responsive to said oscillator and said voltage source for generating one or more voltages of magnitude higher than that supplied by said voltage source and for supplying said higher voltage(s) to said output stage whereby tissue stimulating pulses of voltage magnitude higher than that supplied by said voltage source are provided.

Although this invention is of especial use for cardiac pacemakers, it is not restricted to such use and could be employed for controlling other body functions.

BRIEF DESCRIPTION OF THE DRAWING

Preferred features of the invention are illustrated with reference to the accompanying drawing, which schematically illustrates an electrical circuit diagram of a programmable fixed-rate implanted cardiac pacemaker according to the invention.

BEST MODE OF CARRYING OUT THE INVENTION

Referring to the drawing, the pacemaker comprises an oscillator 2 which drives a ripple counter 4. An output of the ripple counter (which may actually be the combination of several stages of the counter) supplies an output line 6. The oscillator frequency and the ripple counter output selected provide signals on line 6 at an appropriate body stimulation pulse frequency. Line 6 is connected to an output amplifier (within the block formed by the dashed line 14), from whence amplified stimulating pulses are passed to a connection 16 which itself is connected to the active stimulating electrode (not shown) disposed in or on the heart. Line 6 is also connected to a delay unit 18 which, after an appropriate time, resets the counter 4, to enable the next appropriately timed pulse to be transmitted.

The output amplifier 14 includes an output transistor 26, across which is connected a capacitor 28. One end of the latter is connected to the rail $V_{DD}$ of the supply voltage. The other end of capacitor 28 and the emitter of transistor 26 are connected to a chain of Schottky diodes 30, 32, 34, and 36 (Schottky diodes are chosen for their low voltage drop when forward-biased). The cathode of diode 32 is connected to the rail $V_{SS}$ of the supply voltage. For the purposes of illustration, the supply voltage $V_{SS}-V_{DD}$ is about 3 volts. The output of oscillator 2 is supplied to an inverter 38 and via a NAND gate 40 to a second inverter 42. The inverters feed, respectively, capacitors 44 and 46 which lead into the diode chain as illustrated. NAND gate 40 is supplied with a further input, which is from a control line 22 from a pacemaker program store 20.

The pacemaker program store 20 holds a binary bit of information which is transmitted on line 22 for voltage multiplication purposes as to be described. A receiver/decoder 24 is arranged to receive and decode data signals transmitted from outside the patient's body to the implanted pacemaker, and to employ the decoded signals for changing the pacemaker program held in program store 20. For the purposes of illustration, the receiver/decoder 24 and store 20 have been depicted very simply and as providing an output for selecting only the stimulating pulse amplitude. In practice it would be desirable to make these features much more sophisticated so that the program store is employed to provide a varying control for several different pacemaker parameters (e.g. not only pulse amplitude, but also pulse rate, pulse width, hysteresis). The data signals may be transmitted to the receiver/decoder 24 by any suitable means, but preferably we employ data signals transmitted by tone burst modulation (a carrier frequency being pulse width modulated). A receiver/decoder and program store for such data signals is described in copending Application No. 917,130 filed on even date.

Many of the pacemaker components described are constructed as a MOS integrated circuit, and this has been indicated by the block formed by the dashed line 50. The integrated circuit is supplied as is customary, with $V_{DD}$ and $V_{SS}$, but it will be observed that the output transistor 26 of amplifier 14 is connected across $V_{DD}$ and $V_{SS}$ in series with the diode chain and with capacitor 28 in parallel.

The pacemaker operates as follows. Each pulse on output line 6 at the selected rate is passed to output amplifier 14 where it is amplified and conducted to the heart; it is also conducted to delay unit 18. After an appropriate delay corresponding to the pacing pulse width desired, delay unit 18 resets counter 4 and the count then commences in counter 4 for the next appropriately timed pulse to be issued.

In the normal operation $V_{DD}$ is essentially the circuit ground by reason of being connected to the pacemaker indifferent electrode and $V_{SS}$ is supplied at about 3 volts. This 3 volt supply is sufficient for the integrated circuit 50, but insufficient for the output amplifier 14, which in conventional practice needs to generate stimulating pulses of at least about 5 volts for satisfactory pacing. It will be assumed that normally about 5 volts is desired for each pacing pulse but that, under certain circumstances, larger pacing pulses (of about 7.5 volts) are required. The manner in which the approximately 5 volt pulses are generated will first be described, and then the manner in which the 7.5 volt pulses are generated.

For 5 volt stimulating pulses, a "0" is held in program store 20 and is supplied on line 22 to NAND gate 40. The output of NAND gate 40 will be high and point $V_T$ (between inverter 42 and capacitor 46) will always be low. $V_T$ will therefore not manifest the oscillator square wave output. On the other hand, point $V_D$ (between inverter 38 and capacitor 44) will manifest the square wave output of oscillator 2. Point "X", at the junction of diodes 30, 32, 36 will, in the absence of the oscillator square wave pulse train and ignoring the voltage drop across diode 32, normally be held at $V_{SS}(-3$ volts). Capacitor 28 charges to $-3$ volts via diodes 30 and 32. When $V_D$ goes to its most positive due to the square wave pulse train supplied by oscillator 2, a 3 volt drop will exist across capacitor 44 and the latter will charge via diode 32. When $V_D$ goes negative due to the oscillator pulse train, point X goes further negative. At this time diode 30 is forward-biased and it conducts, causing capacitor 28 to acquire an amount of charge due to the sharing of charge between capacitors 44 and 28. Taking into account diode voltage drops and assuming that no current is being drawn from the output amplifier circuit (no pacing pulse being issued), capacitor 28 will charge to about 5 volts over several cycles of the oscillator pulse train and it will hold its charge until a pacing pulse is transmitted to the output amplifier 14 from the integrated circuit 50. With no current being drawn from the output transistor 26, and hence no potential drop across its collector resistor, the 5 volt potential held by capacitor 28 appears directly across output transistor 26 and hence the amplitude of the pacing pulse transmitted to the active electrode at connection 16, when this transistor is switched on, is at about 5 volts rather than the 3 volts supplied by $V_{DD}/V_{SS}$. It will be appreciated that capacitor 28 will charge to 5 volts gradually over several cycles of the oscillator frequency, but provided that the latter frequency is much higher than the stimulating pulse frequency, capacitor 28 will always be charged to 5 volts ready for discharge on the next pacing pulse.

When pacing pulses of about 7 volts magnitude are desired, a "1" is held in program store 20 and is supplied on line 22 to NAND gate 40. The output downstream of inverter 42 (at $V_T$) is the oscillator square wave pulse train but in anti-phase to the similar pulse train at $V_D$.

Under such circumstances, when $V_D$ goes negative, point X goes further negative, as previously explained, and $V_T$ will be positive, charging capacitor 46 (to about $-5$ volts). When $V_D$ goes positive, $V_T$ will go negative and capacitor 46 will share its charge with capacitor 28. The effect is for capacitor 28 to charge to a higher voltage than it would have done if charged only from capacitor 44. Taking into account diode drops, and assuming that no current is drawn from output transistor 26, capacitor 28 will charge, over several cycles of the oscillator pulse train, to a potential difference of about 7.5 volts. When a pacing pulse is transmitted to the output amplifier 14, this 7.5 volts is employed to provide a pacing pulse to connection 16 of corresponding magnitude.

It will thus be appreciated that the presence of a "0" or "1" on line 22 controls the magnitude of the pacing pulses.

Although the above embodiment relates to a fixed-rate cardiac pacemaker, it will be appreciated that this is only given for the purposes of example, and the invention is equally-applicable to demand cardiac pacemakers, or to body function control apparatus employed to provide stimulating pulses of varying amplitude to other parts of the body.

What is claimed is:

1. In a programmable pacer system having a remote source of program control signals, an implantable pacer comprising:
   (a) a voltage supply;
   (b) oscillator means for producing a pulse signal having a fixed frequency;
   (c) counter means for generating a pacer output control signal upon each occurrence of a predetermined plurality of oscillator pulses;
   (d) memory means for receiving from said source and for storing a program control signal representative of a desired multiplication factor of said supply voltage for pacer stimulation signals;
   (e) output means, responsive to said output control signal, for generating pacer stimulation signals, said output means including:
      (i) a first capacitor coupled on one side to said supply, and
      (ii) transistor means, connected in parallel with said capacitor and enabled by said output control signal, for generating stimulation signals having an amplitude of the voltage on said capacitor at the time of occurrence of said control signal;
   (f) capacitor means, enabled by said stored program control signal, and charged by a plurality of successive excursions in one direction of said oscillator pulse signal, for supplying added charge increments to the other side of said first capacitor during successive excursions in the opposite direction of said oscillator pulse signal.

2. A pacer as described in claim 1 wherein said capacitor means includes a plurality of capacitors, in parallel with one another, and switching means, controlled by said memory means, for selectively coupling at least one of said plurality of capacitors to said oscillator and for alternately charging and at least partly discharging said at least one capacitor at the rate of the pulse signal produced by said oscillator means, thereby correspondingly altering said supplying of charge to said first capacitor, and in turn altering the amplitude of said stimulator signals.

3. A pacer as described in claim 2 wherein said capacitor means further includes a plurality of diodes connected with said other side of said first capacitor, and closing a circuit with said supply, said plurality of capacitors being respectively coupled to respective nodes intermediate said diodes.

* * * * *